(12) United States Patent
Cabon et al.

(10) Patent No.: US 10,781,157 B2
(45) Date of Patent: Sep. 22, 2020

(54) PROCESS FOR PREVENTING THE DEPOSITION OF POLYMERS IN A PROCESS FOR PURIFYING (METH)ACRYLIC ACID

(71) Applicant: Arkema France, Colombes (FR)

(72) Inventors: Yves Cabon, Metz (FR); Christian Tragus, Morsbach (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/465,171

(22) PCT Filed: Dec. 6, 2017

(86) PCT No.: PCT/FR2017/053414
§ 371 (c)(1),
(2) Date: May 30, 2019

(87) PCT Pub. No.: WO2018/104661
PCT Pub. Date: Jun. 14, 2018

(65) Prior Publication Data
US 2020/0002262 A1    Jan. 2, 2020

(30) Foreign Application Priority Data
Dec. 8, 2016  (FR) .................... 16 62118

(51) Int. Cl.
*C07C 51/50* (2006.01)
*C07C 51/48* (2006.01)
*C07C 57/04* (2006.01)

(52) U.S. Cl.
CPC .............. *C07C 51/50* (2013.01); *C07C 51/48* (2013.01); *C07C 57/04* (2013.01)

(58) Field of Classification Search
CPC .......... C07C 57/04; C07C 51/48; C07C 51/50
See application file for complete search history.

(56) References Cited

U.S. PATENT DOCUMENTS

| 5,728,872 A | 3/1998 | Riemenschneider |
| 6,888,026 B2 | 5/2005 | Sakamoto et al. |
| 7,005,544 B2 | 2/2006 | Ohkouchi et al. |
| 2003/0127315 A1* | 7/2003 | Kroker ............... B01D 1/065 203/29 |
| 2004/0044120 A1* | 3/2004 | Ohkouchi ............ C07C 51/46 524/556 |
| 2004/0249202 A1* | 12/2004 | Hirao ............... B01D 53/1487 562/545 |
| 2007/0106093 A1* | 5/2007 | Fauconet ............. C07C 57/04 562/600 |
| 2012/0085969 A1 | 4/2012 | Blum et al. |
| 2016/0090347 A1 | 3/2016 | Hammon et al. |
| 2017/0166507 A1* | 6/2017 | Devaux ............... C07C 67/58 |

FOREIGN PATENT DOCUMENTS

| GB | 1 127 127 | 9/1968 |
| WO | WO 2008/033687 A2 | 3/2008 |
| WO | WO-2015124856 A1 * | 8/2015 ............. C07C 45/52 |

OTHER PUBLICATIONS

Culp et al. (Propane to Acrylic acid, Univ. Penn. ScholarlyCommons, pp. 1-231, Published 2013) (Year: 2013).*

* cited by examiner

*Primary Examiner* — Yevgeny Valenrod
*Assistant Examiner* — Blaine G Doletski
(74) *Attorney, Agent, or Firm* — Lynn B. Morreale

(57) ABSTRACT

This invention produces technical (meth)acrylic acid without being confronted with problems of fouling of systems to purify the crude reaction mixture of (meth)acrylic acid synthesis, due to the presence of glyoxal formed during synthesis. The invention is based on the addition or generation of quinoline derivative in a glyoxal-containing (meth) acrylic acid flow in a quinoline/glyoxal derivative molar ratio ranging from 0.1 to 5, during the purification steps, said quinoline compound with one of formulas (I) or (II):

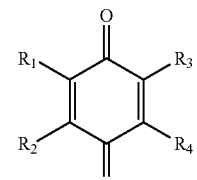

(I)

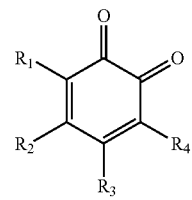

(II)

wherein, groups $R_1$, $R_2$, $R_3$, and $R_4$ independently denote a hydrogen atom or a $C_1$-$C_6$, or $R_1$ et $R_2$ C-alkyl group combine and together with the atoms to which they are attached, form a saturated or unsaturated ring or heterocycle, preferably a phenyl group, and/or $R_3$ and $R_4$ combine and with the atoms to which they are attached, form a saturated or unsaturated ring or heterocycle, preferably a phenyl group.

14 Claims, No Drawings

PROCESS FOR PREVENTING THE DEPOSITION OF POLYMERS IN A PROCESS FOR PURIFYING (METH)ACRYLIC ACID

CROSS-REFERENCE TO RELATED APPLICATIONS

This application is a national stage application under 35 U.S.C. § 371 of PCT/FR2017/053414, filed Dec. 6, 2017 which claims benefit to application FR 16 62118, filed Dec. 8, 2016.

TECHNICAL FIELD

The present invention relates to the manufacture of (meth) acrylic acid, and its purpose is the reduction of fouling during the purification of (meth)acrylic acid containing glyoxal.

The invention is based on the use of a quinoline derivative to limit the formation of polymers in a liquid phase containing (meth)acrylic acid and glyoxal.

PRIOR ART AND TECHNICAL PROBLEM

Industrial processes for synthesizing acrylic acid generally lead to a gaseous reaction medium consisting of acrylic acid and a complex mixture of impurities. These impurities are generally classified according to their ability to be condensed in a liquid mixture, or absorbed in a liquid mixture, or classified according to their boiling point in relation to that of acrylic acid (lighter compounds, or heavier compounds).

As a result, the purification steps on an industrial acrylic acid manufacturing unit usually use a set of operations to separate and recover acrylic acid contained in this gaseous effluent.

Some of these operations use one or more organic or aqueous solvents as absorption agents (gas-liquid exchanges) and/or as extraction agents in liquid medium (liquid-liquid exchanges), and/or as agents for separation by azeotropic distillation. These methods also include solvent recovery and purification steps, and necessarily involve a large number of distillation columns, operating at elevated temperatures, to yield a technical acrylic acid, in which the impurity content has been greatly reduced. These methods are widely described in the state of the art.

Other simplified processes very significantly reduce the number of unit operations required to obtain purified acrylic acid by not involving any addition of organic solvent external to the process, and by using a limited number of distillation columns. These simplified processes enable the obtention of a high purity quality technical acrylic acid. For example, the method described in EP 2066613, based on the use of a dewatering column and a finishing column, or the method described in US 2016/0090347 based on a partial condensation method using two columns.

Certain impurities like aldehydes, including furfuraldehyde, benzaldehyde, acrolein, or glyoxal, are difficult to separate from acrylic acid, and require further purification of the technical acrylic acid in order to eliminate them up to an in-depth level. This additional purification, generally carried out with the aid of chemical agents or by fractional crystallization, leads to a high purity acrylic acid grade, generally known as glacial acrylic acid or polymer grade acrylic acid used in the production of flocculants.

All of these acrylic acid purifying processes have in common the addition of polymerisation inhibitors at different purification stages to prevent the formation of polymers resulting from the polymerisation of acrylic acid, and/or by-products, and avoid fouling the purification units, especially distillation units. The addition of polymerization inhibitor is also necessary to stabilize the acrylic acid during its transportation and storage.

Thus, nitroxide-type polymerization inhibitors have been proposed in patent number FR1520290, these compounds having a stabilizing property clearly superior to that of conventional inhibitors such as hydroquinone or benzoquinone.

In patent document EP 765 856, a synergy between a compound with a stable nitroxyl radical, such as 4-hydroxy-2,2,6,6-tetramethylpiperidinoxyl, and a dihetero-substituted benzene compound having at least one transferable hydrogen atom, in particular hydroquinone methyl ether, has been demonstrated for the stabilization of acrylic acid compositions.

It is a well-known fact that one of the delicate points in the manufacture of (meth) acrylic monomers stems from the fact that these compounds are relatively unstable and evolve easily into polymer formation. This evolution is favoured by the effect of temperature, and is therefore particularly easy in the purification steps of these monomers, for example during the distillation operations. The usual consequence of this process is the deposit in the plant equipment, of solid polymers that eventually cause clogging requiring a stoppage of the workshop for cleaning, which is difficult and expensive in non-productive downtime.

To reduce these disadvantages, polymerization inhibitors are conventionally added to the flows, generally at head-end distillation columns, condensers, etc. which may be centre for a liquid-vapour balance leading to the condensation of flows rich in (meth) acrylic monomer.

However, despite the use of polymerization inhibitors, acrylic acid purification operations are often accompanied by the formation of insoluble polymers in the medium which precipitate in the form of a solid deposit.

This problem has been particularly noted when the flow of acrylic acid stabilized with at least one polymerization inhibitor contains glyoxal as an impurity, even at very low levels.

Manufacturers are thus confronted with the sensitivity of acrylic acid to polymerization in the presence of impurities such as glyoxal. This results in fouling of crude acrylic acid flow purification systems until technical acrylic acid is obtained. These fouling problems cause the shut-down of the purification units and a loss in productivity.

Various solutions have already been proposed in the prior art to resolve this issue.

Patent application US 2012/0085969, proposes the addition of a compound comprising copper, for example a copper salt at an oxidation level of +2 or +1, in liquid phase comprising at least 10% weight of acrylic acid comprising at least 100 ppm of propionic acid and 100 ppm of glyoxal in relation to the weight of acrylic acid. Under these conditions, the tendency to polymerize the liquid phase is significantly reduced. However, this method has the disadvantage of using a heavy metal compound such as copper.

In the patent EP 1 298 120, proposals are made to treat the flow of acrylic acid by reverse osmosis, to reduce the concentration of glyoxal contained in the permeation liquid to a content of less than 0.03% by mass. This type of permeation treatment is expensive in terms of investment and maintenance (changing membranes) and can be difficult to implement on a charged flow.

In patent number EP1396484, the polymerization of acrylic acid in an aqueous solution of acrylic acid containing glyoxal and/or its hydrate is inhibited by controlling the water content in certain theoretical trays of the distillation column used to dehydrate the aqueous solution with the aid of an azeotropic solvent.

The process of patent number EP 1396484 only applies to the dehydration step in a recovery/purification process comprising the absorption of acrylic acid in the form of an aqueous solution, and consists in eliminating more than 50% of the glyoxal present in the aqueous solution of acrylic acid from the dehydration column; a compound inhibiting the polymerization of acrylic acid may be added to the dehydration column. These include, for example, hydroquinone, hydroquinone methyl ether, phenothiazine, or a 2,2,6,6-tetramethylpiperidinoxyl derivative, or mixtures thereof.

The processes of the prior art still have many disadvantages, so there is still a need to effectively eliminate the risks related to the fouling of acrylic acid purification plants when the acrylic acid contains glyoxal.

Inventors have made a surprising discovery that the use of benzoquinone or a quinoline derivative provides the possibility of responding to this need. It has thus been found that the presence of benzoquinone in a flow of acrylic acid with a low glyoxal content effectively inhibits the polymerization of acrylic acid, and reduces the fouling phenomena on the acrylic acid purification plants. The same effect also emerged for methacrylic acid which also has an increased risk of polymerisation in the presence of glyoxal.

Quinol derivatives, in particular 1,4-benzoquinone, are generally known as polymerization inhibitors, but their particular effect on the inhibition of the polymerization of (meth)acrylic acid in the presence of glyoxal has never been described.

Consequently, the invention proposes to provide a simple solution, that is easy to implement to maintain a high productivity of (meth)acrylic acid production processes.

SUMMARY OF THE INVENTION

The subject of the present invention is a process for preventing the deposition of polymeric compounds during the purification operations of (meth)acrylic acid, characterized in that at least one flow of (meth)acrylic acid is added, containing at least one glyoxal as impurity, at least one quinolic derivative corresponding to one of formulas (I) or (II):

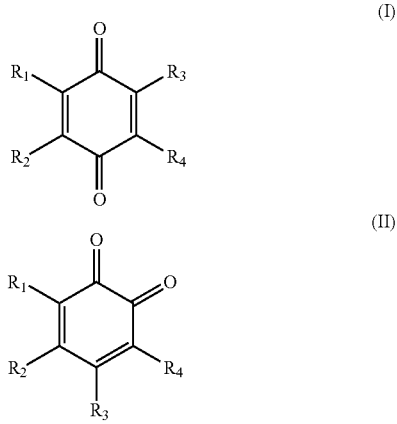

wherein, groups $R_1$, $R_2$, $R_3$, and $R_4$ independently denote a hydrogen atom or a $C_1$-$C_6$, or $R_1$ et $R_2$ C-alkyl group combine and together with the atoms to which they are attached, form a saturated or unsaturated ring or heterocycle, preferably a phenyl group, and/or $R_3$ and $R_4$ combine and with the atoms to which they are attached, form a saturated or unsaturated ring or heterocycle, preferably a phenyl group.

According to the invention, in order to obtain the desired effect, said quinoline derivative must be added at a content expressed by the quinoline/glyoxal derivative molar ratio of between 0.1 and 5.

The quinoline derivative is a compound selected from cyclic conjugated ethylenic diketones. The quinoline derivative may be selected for example from 1,2-benzoquinone, 1,4-benzoquinone, naphthaquinone and anthraquinone.

According to one embodiment of the invention, the quinoline derivative is introduced directly in liquid form, in solution in an aqueous solvent, or in solution in (meth)acrylic acid.

According to one embodiment of the invention, the quinoline derivative is generated in situ in said (meth)acrylic acid flow.

According to the invention, the (meth)acrylic acid may be of petrochemical origin or at least partly of renewable origin.

"Purification operation" refers to any step intended to modify the composition of the flow of (meth)acrylic acid of origin, for example during a separation operation of light by-products or heavy by-products, or during a dehydration operation. The purification operations may generally comprise distillations, liquid/liquid extractions, liquid/gas exchanges, film evaporator separation, or crystallizations.

According to the invention, the flow of (meth)acrylic acid contains at least glyoxal, it being understood that the term "glyoxal" includes glyoxal of formula $C_2O_2H_2$ (ethanedial), as well as its derivatives which can be formed in situ in (meth)acrylic acid synthesis/purification process, particularly in the form of substituted glyoxal (for example methylglyoxal), or in the form of monomeric or polymeric hydrates.

The invention also relates to the use of at least one quinoline derivative to limit fouling problems during the purification of (meth)acrylic acid flow comprising at least glyoxal as impurity.

The invention further relates to a process for purifying (meth)acrylic acid, characterized in that it comprises the addition of at least one quinolic derivative in a flow comprising at least (meth) acid acrylic and at least glyoxal.

Another subject of the invention relates to a process for producing (meth)acrylic acid, characterized in that it comprises the said purification process.

The invention will be more fully described in the description which follows.

DETAILED PRESENTATION OF THE INVENTION

The purpose of the invention is to produce technical (meth)acrylic acid without being confronted with the problem of fouling of the systems used to purify the crude reaction mixture of (meth)acrylic acid synthesis, in particular due to the presence of glyoxal formed during the synthesis process.

The invention is based on the addition of a quinoline derivative corresponding to one of the formulas (I) or (II) in a (meth)acrylic acid flow containing glyoxal during the purification steps, the quinoline/glyoxal derivative molar ratio being between 0.1 and 5.

The term "(meth)acrylic acid" includes acrylic acid and methacrylic acid. Preferably, the (meth)acrylic acid is acrylic acid.

The (meth)acrylic acid may be of petrochemical origin or at least partly of renewable origin.

According to one embodiment of the invention, acrylic acid is derived from a production process using propylene or propane as a raw material.

According to one embodiment of the invention, acrylic acid is obtained from a process using ethylene and $CO_2$ as raw materials.

According to one embodiment of the invention, acrylic acid is derived from a process using acetic acid as raw material.

According to one embodiment of the invention, the methacrylic acid is obtained from isobutylene and/or tert-butanol, butane and/or isobutane.

According to one embodiment of the invention, acrylic acid is derived from a production process using glycerol or glycerine as raw material.

According to one embodiment of the invention, the acrylic acid is derived from a process for the dehydration of lactic acid or ammonium lactate, or of a process for the dehydration of 3-hydroxypropionic acid or of its ammonium salt. These compounds may be derived from the fermentation of biomass and/or sugars.

The above mentioned synthesis processes all lead to the formation of crude (meth)acrylic acid, meaning to a reaction mixture constituted, apart from (meth)acrylic acid:

- of incondensable light compounds under commonly used temperature and pressure conditions: nitrogen, unconverted oxygen, carbon monoxide and carbon dioxide formed in small quantities by ultimate oxidation or rotating in a circle, by recycling, in the process,
- of condensable light compounds: in particular water, generated by the synthesis reaction or as diluent, unconverted acroleine light aldehydes, such as formaldehyde, acetaldehyde and glyoxal, formic acid and acetic acid,
- heavy compounds: furfuraldehyde, benzaldehyde, maleic acid and anhydride, benzoic acid, 2-butenoic acid, phenol, protoanemonin.

By definition, a light compound is a compound whose boiling point is lower than that of (meth)acrylic acid under the pressure conditions used. A heavy compound is a compound whose boiling point is higher than that of (meth) acrylic acid under the pressure conditions used.

In the following description of the invention, for the sake of simplification, reference will be made to acrylic acid only, but the characteristics and advantages of the invention also apply to methacrylic acid.

The second manufacturing stage involves recovering the acrylic acid contained in the crude reaction mixture to turn it into technical acrylic acid.

According to a first embodiment of the invention, the process for the recovery/purification of acrylic acid comprises the extraction of acrylic acid by counter-current absorption in the form of an aqueous solution of acrylic acid, generally followed by a dehydration step which is carried out in the presence of an acrylic acid solvent immiscible with water, but may in combination with water, form an azeotrope. A dehydration step by azeotropic distillation with the solvent enables the obtention of a separation of water effective and less expensive energy. It may also be coupled with liquid-liquid extraction separation.

According to a second embodiment of the invention, the process for the recovery/purification of acrylic acid comprises the extraction of acrylic acid by counter-current absorption using a hydrophobic heavy solvent, generally followed by the separation by distillation of a mixture containing acrylic acid solution in the hydrophobic heavy solvent.

These acrylic acid recovery/purification processes which furthermore carry out several distillation steps to eliminate the light and/or heavy compounds, are known in the prior art, and are for example described in patent documents WO10/031949 and WO11/114051 relating to the synthesis of acrylic acid from glycerol, to which reference may be made in the context of the present invention.

According to another embodiment of the invention, the process for recovering/purifying acrylic acid does not use an external organic solvent. For example, the process as described in patent EP 2066613 B1 may be used, with just two distillation columns—a dehydration column and a finishing column—without introducing a solvent. Alternatively, the partial condensation method described in US2016/090347 may be used.

Whatever the recovery/purification process used to recover technical acrylic acid, the glyoxal present as impurity in the medium to be treated is found in different flows during the various process operations. Indeed, it is a rather light compound, most of which is eliminated at the same time as acetic acid, but a sufficiently large part also distils with acrylic acid.

The flow of acrylic acid into which a quinoline derivative is introduced to prevent the formation of insoluble polymers is preferably a liquid flow.

This liquid flow may be a distillation column feed flow, or a distillation column condensate, or a distillation column reflux, in the purification process.

Said acrylic acid flow generally comprises at least 10% by weight of acrylic acid, preferably at least 30% by weight, in particular at least 50% by weight of acrylic acid, and may comprise up to 99.5% by weight of acrylic acid.

Said flow of acrylic acid further comprises at least 10 ppm of glyoxal, and may comprise a glyoxal content ranging from 10 to 5000 ppm.

The acrylic acid content in the flows may be determined by gas phase or liquid phase chromatography and the glyoxal content can be determined by liquid chromatography.

Said flow of acrylic acid may furthermore comprise at least one polymerization inhibitor, for example in particular from 50 ppm to 5% by weight, in particular from 0.01% to 3% by weight, relative to the medium containing the acrylic acid. The polymerisation inhibitor(s) may be selected from phenolic derivatives such as hydroquinone and its derivatives like hydroquinone methyl ether; 2,6-di-tert-butyl-4-methylphenol (BHT); and 2,4-dimethyl-6-tert-butylphenol (Topanol A); phenothiazine and its derivatives; manganese salts, such as manganese acetate; thiocarbamic or dithiocarbamic acid salts, such as metal thiocarbamates and dithiocarbamates, like copper di-n-butyldithiocarbamate; N-oxyl compounds, as 4-hydroxy-2,2,6,6-tetramethylpiperidinoxyl (4-OH-TEMPO); compounds having nitroso groups, including N-nitroso phenylhydroxylamine and its ammonium salts; amine compounds such as para-phenylenediamine derivatives.

According to a particular embodiment of the invention, the flow of acrylic acid comprises phenothiazine as a polymerization inhibitor, at a content ranging from 50 ppm to 5% by weight, especially from 100 ppm to 1% by weight.

The quinoline derivative corresponding to one of formulas (I) or (II) above is generally introduced in liquid form, in solution in an aqueous solvent, or in solution in acrylic acid.

1,4-Benzoquinone is preferably used as quinoline compound.

Alternatively, the quinoline derivative may be generated in situ in the acrylic acid flow, in particular from a hydroquinone derivative or a catechol derivative, and an oxidizing compound, according to the following reaction schemes:

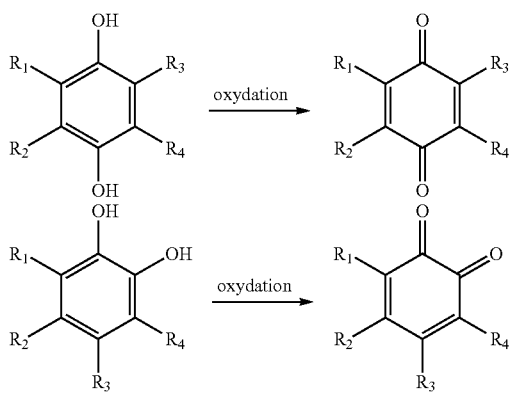

wherein, groups $R_1$, $R_2$, $R_3$ and $R_4$ meet the definitions defined above.

According to one embodiment, groups $R_1$ to $R_4$ are the hydrogen atom, the in situ quinoline derivative generation being made from hydroquinone or catechol.

This embodiment may be advantageous in order to avoid the delicate handling of certain quinol derivatives.

Oxidation may be carried out using an oxidizing compound selected, for example, from metal salts, especially manganese or copper salts, or N-oxyl derivatives, in particular 4-OH-Tempo.

According to a preferred embodiment of the invention, 1,4-benzoquinone is generated in situ by oxidation of the hydroquinone using an oxidizing compound such as 4-OH-Tempo, according to the following reaction:

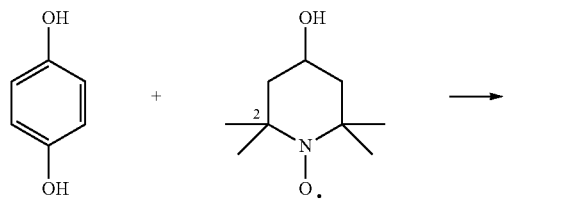

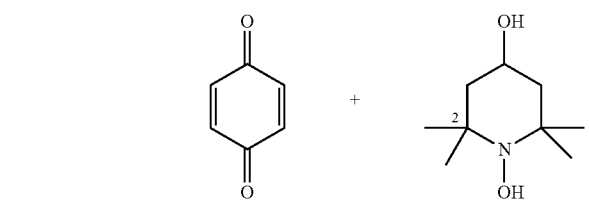

The hydroxyl by-product generated at the same time as benzoquinone does not distil with acrylic acid because it is a higher boiling point compound, hence, it does not pollute the final technical acrylic acid.

This embodiment is particularly advantageous because hydroquinone is a polymerization inhibitor widely used in acrylic acid manufacturing processes, and may already be present in the various acrylic acid flows comprising glyoxal. The formation of polymeric deposits during acrylic acid purification operations can be avoided by simply adding 4-OH-Tempo, in the form of a low-toxicity aqueous solution commercially available, with benzoquinone being generated in situ.

The quinoline derivative content introduced into the acrylic acid flow to prevent fouling of the plant, expressed by quinoline/glyoxal derivative molar ratio is between 0.1 and 5. Preferably quinoline derivative is introduced so that quinoline/glyoxal molar ratio is between 0.2 and 5, preferably between 0.2 and 3, in particular between 0.5 and 2.

According to a preferred embodiment of the invention a quinoline derivative, preferably 1,4-benzoquinone is introduced, or generated in situ.

According to a preferred embodiment of the invention, a quinoline derivative, preferably 1,4-benzoquinone, is introduced into or generated in situ to feed the distillation column(s) in which acetic acid and glyoxal is concentrated in a process for producing acrylic acid from propylene.

According to a preferred embodiment of the invention, a quinoline derivative, preferably benzoquinone, is introduced into an acrylic acid flow comprising from 90 to 99.5% by weight of acrylic acid, from 10 to 1000 ppm glyoxal and 100 to 10,000 ppm phenothiazine.

The acrylic acid purifying process according to the invention comprising the adding of at least one quinoline derivative in a flow containing at least acrylic acid and at least glyoxal, can easily be part of any acrylic acid synthesis process.

The following examples illustrate the present invention without limiting its scope.

EXPERIMENTAL PART

The following abbreviations are used in the examples:
BQ: 1,4-benzoquinone (CAS 106-51-4)
NQ: Naphthalene (CAS 130-15-4)
HQ: hydroquinone (CAS 123-31-9)
PTZ: phenothiazine (CAS 92-84-2)
4HT: 4-OH-Tempo (CAS 2226-96-2)

Example 1

500 g of glacial acrylic acid was placed in a 2 litre flask and supplemented with 1000 ppm phenothiazine (PTZ).

Various additions of glyoxal, in its commercial form of 40% by weight aqueous solution, were made, and the effect of different compounds in this medium was observed under the following conditions:

The medium was placed in an oil bath at 110° C. under 230 mbar for 2 h. A 5 ml/min air bubble was applied for the duration of the experiment. At the end of the experiment, the liquid phase was emptied and any solids present were recovered, dried under vacuum and weighed.

The various tests are summarised in table 1 below.

TABLE 1

| Testing | | Glyoxal added (µl of 40% aqueous solution) | Glyoxal added mmol/l | Added compound(s) Type | Quantity (ppm) | Amount (mmol/l) | Mass of solid measured (g) |
|---|---|---|---|---|---|---|---|
| 1 | references | 0 | 0 | / | 0 | | 0 |
| 2 | | 20 | 0.37 | / | 0 | | 1 |
| 3 | | 50 | 0.93 | / | 0 | | 11 |
| 4 | | 100 | 1.86 | / | 0 | | >40 |
| 5 | comparative | 50 | 0.93 | PTZ | 20 | 0.11 | 13 |
| 6 | | 50 | 0.93 | PTZ | 50 | 0.26 | 15 |
| 7 | | 50 | 0.93 | PTZ | 100 | 0.53 | 15 |
| 8 | | 100 | 1.86 | PTZ | 100 | 0.53 | >40 |
| 9 | | 100 | 1.86 | PTZ | 200 | 1.06 | >40 |
| 10 | | 100 | 1.86 | PTZ | 500 | 2.64 | >40 |
| 11 | | 50 | 0.93 | HQ | 20 | 0.19 | 11 |
| 12 | | 50 | 0.93 | HQ | 50 | 0.48 | 10 |
| 13 | | 50 | 0.93 | HQ | 100 | 0.95 | 10 |
| 14 | | 100 | 1.86 | HQ | 100 | 0.95 | >40 |
| 15 | | 100 | 1.86 | HQ | 200 | 1.91 | >40 |
| 16 | | 100 | 1.86 | HQ | 500 | 4.77 | >40 |
| 17 | | 50 | 0.93 | 4HT | 20 | 0.11 | 11 |
| 18 | | 50 | 0.93 | 4HT | 50 | 0.29 | 11 |
| 19 | | 50 | 0.93 | 4HT | 100 | 0.57 | 10 |
| 20 | | 100 | 1.86 | 4HT | 100 | 0.57 | >40 |
| 21 | | 100 | 1.86 | 4HT | 200 | 1.14 | >40 |
| 22 | | 100 | 1.86 | 4HT | 500 | 2.85 | 35 |
| 23 | invention | 50 | 0.93 | BQ | 20 | 0.19 | 4 |
| 24 | | 50 | 0.93 | BQ | 50 | 0.49 | 0.7 |
| 25 | | 50 | 0.93 | BQ | 100 | 0.97 | 0.3 |
| 26 | | 100 | 1.86 | BQ | 100 | 0.97 | 25 |
| 27 | | 100 | 1.86 | BQ | 200 | 1.94 | 0.5 |
| 28 | | 100 | 1.86 | BQ | 500 | 4.86 | 0.2 |
| 29 | | 100 | 1.86 | NQ | 150 | 1.00 | 14 |
| 30 | | 100 | 1.86 | NQ | 300 | 1.99 | 2 |
| 31 | invention | 50 | 0.93 | HQ | 100 | 0.95 | 7 |
| | | | | 4HT | 50 | 0.29 | |
| 32 | | 50 | 0.93 | HQ | 100 | 0.95 | 3 |
| | | | | 4HT | 100 | 0.57 | |
| 33 | | 50 | 0.93 | HQ | 100 | 0.95 | 0.4 |
| | | | | 4HT | 200 | 1.14 | |
| 34 | | 50 | 0.93 | HQ | 100 | 0.95 | 0.3 |
| | | | | 4HT | 500 | 2.85 | |
| 35 | | 100 | 1.86 | HQ | 200 | 1.91 | 35 |
| | | | | 4HT | 200 | 1.14 | |
| 36 | | 100 | 1.86 | HQ | 200 | 1.91 | 0.7 |
| | | | | 4HT | 500 | 2.85 | |

The presence of more or less significant amounts of solids in the medium makes it possible to characterise the probability of fouling on an industrial scale.

As shown in reference tests 1 to 4, polymerisation of acrylic acid occurs when glyoxal is present in the medium, even in the presence of 1000 ppm PTZ.

The addition of an additional amount of PTZ (tests 5 to 10) does not prevent the polymerization of acrylic acid.

With a separate addition of hydroquinone or 4-OH-Tempo, even at 500 ppm in acrylic acid, the formation of insoluble solids in the medium was noticed (tests 11 to 22).

Benzoquinone and naphthaquinone have sufficiently inhibited the polymerization of acrylic acid to prevent the formation of insoluble solids that can lead to fouling of the plant (tests 23 to 30).

The simultaneous addition of hydroquinone and 4-OH-Tempo in proportions enabling the generation of benzoquinone in situ at different levels leads to the same result (tests 31 to 36).

Example 2: Use of Benzoquinone as-it, Continuous Test

An industrial flow of acrylic acid containing about 50 ppm of glyoxal (0.91 mmol/l), 200 ppm HQ (1.91 mmol/l) and supplemented with 1000 ppm of PTZ was injected at a rate of 100 g/h in a glass thermosiphon reboiler of approximately 200 ml, surmounted by a total reflux condenser and equipped with an overflow (i.e. a residence time of 2 h). The reboiler operates at 110° C. in the liquid under a pressure of 380 mbar. The fouling of the reboiler was visually observed, in the absence of benzoquinone, and in the presence of 100 or 200 ppm of benzoquinone (respectively 0.97 mmol/l and 1.94 mmol/l).

After 1.5 hours of operation in the absence of benzoquinone, the experiment had to be stopped due to heavy fouling of the reboiler.

In the presence of benzoquinone, the experimental set-up was still clean after 8 hours of experience.

Example 3: Use of the In Situ Generated Benzoquinone, Continuous Test

An industrial flow of acrylic acid containing about 50 ppm of glyoxal (0.91 mmol/l), 200 ppm HQ (1.91 mmol/l) and supplemented with 1000 ppm of PTZ was injected at a rate of 100 g/h in a glass thermosiphon reboiler of approximately 200 ml, surmounted by a total reflux condenser and equipped with an overflow (i.e. a residence time of 2 h). The reboiler operates at 110° C. in the liquid under a pressure of 380 mbar. The fouling of the reboiler was visually observed, without further additions, and adding 200 and 500 ppm of 4-OH-Tempo (respectively 1.14 mmol/l and 2.85 mmol/l), in order to generate benzoquinone in situ from the HQ already contained in the medium.

After 1.5 hours of operation in the absence of 4-OH-Tempo, the experiment had to be stopped because of heavy fouling of the reboiler.

In the presence of 4-OH-Tempo to generate benzoquinone, the experimental set-up was still clean after 8 hours of experience.

The invention claimed is:

1. A process for preventing deposition of polymeric compounds during (meth)acrylic acid purification operations, wherein to at least one (meth)acrylic acid flow containing at least glyoxal as impurity, is added, at least one quinone derivative corresponding to one of formulas (I) or (II):

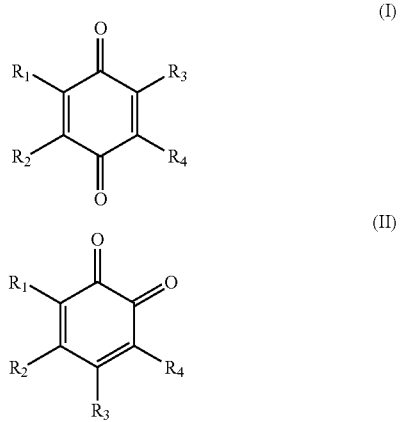

wherein, groups $R_1$, $R_2$, $R_3$, and $R_4$ independently denote a hydrogen atom or a $C_1$-$C_6$, or $R_1$ et $R_2$ C-alkyl group combine and together with the atoms to which they are attached, form a saturated or unsaturated ring or heterocycle, and/or $R_3$ and $R_4$ combine and with the atoms to which they are attached, form a saturated or unsaturated ring or heterocycle, said quinone derivative being added at a content expressed by the quinone/glyoxal derivative molar ratio of between 0.1 and 5.

wherein the quinone derivative is generated in situ in said (meth)acrylic acid flow, from a hydroquinone derivative or a catechol derivative, and an oxidizing compound.

2. The process according to claim 1, wherein the quinone derivative is introduced directly in liquid form, in solution in an aqueous solvent or in solution in (meth)acrylic acid.

3. The process according to claim 1, wherein the quinone derivative is selected from 1,2-benzoquinone, 1,4-benzoquinone, naphthaquinone and anthraquinone.

4. The process according to claim 1, wherein the quinone derivative is 1,4-benzoquinone generated in situ from hydroquinone and 4-hydroxy-2,2,6,6-tetramethyl piperidinoxyl (4-OH-tempo).

5. The process according to claim 1 wherein (meth)acrylic acid is of petrochemical origin.

6. The process according to claim 1 wherein (meth)acrylic acid is at least partially of renewable origin.

7. The process according to that claim 1 wherein said (meth)acrylic acid flow derives from a purification process comprising the extraction of (meth)acrylic acid by counter-current absorption in the form of an aqueous solution of (meth)acrylic acid.

8. The process according to claim 1 wherein said (meth)acrylic acid flow derives from a purification process comprising the extraction of (meth)acrylic acid by counter-current absorption at medium of a hydrophobic heavy solvent.

9. The process according to claim 1 wherein the said (meth)acrylic acid flow derives from a purification process without external organic solvent.

10. The process according to claim 1 wherein said (meth)acrylic acid flow contains at least 10% weight (meth)acrylic acid.

11. The process according to claim 1 wherein said (meth)acrylic acid flow contains at least 10 ppm of glyoxal.

12. The process according to claim 1 wherein said (meth)acrylic acid flow additionally contains at least one polymerization inhibitor.

13. The process according to claim 1 wherein the quinone derivative is added at a content expressed by the molar quinone/glyoxal derivative ratio of between 0.2 and 5.

14. The process according to claim 1 wherein said (meth)acrylic acid flow is a liquid feed flow for a distillation column, a distillation column condensate, or a distillation column reflux.

* * * * *